United States Patent
Shen et al.

(10) Patent No.: US 7,662,860 B2
(45) Date of Patent: Feb. 16, 2010

(54) 3D-STRUCTURE MODEL OF SARS CORONAVIRUS 3CL PROTEASE AND ANTI-SARS DRUGS

(75) Inventors: Jianhua Shen, Shanghai (CN); Hualiang Jiang, Shanghai (CN); Xu Shen, Shanghai (CN); Jianping Zuo, Shanghai (CN); Xiaomin Luo, Shanghai (CN); Donglu Bai, Shanghai (CN); Jingkang Shen, Shanghai (CN); Kaixian Chen, Shanghai (CN); Chunshan Gui, Shanghai (CN); Lili Chen, Shanghai (CN); Jing Chen, Shanghai (CN); Yifu Yang, Shanghai (CN); Xianhan Zhuang, Shanghai (CN); Yiming Yang, Shanghai (CN); Xuchang He, Shanghai (CN); Hong Liu, Shanghai (CN); Bing Xiong, Shanghai (CN); Haibin Luo, Shanghai (CN); Tao Sun, Shanghai (CN); Fei Ye, Shanghai (CN)

(73) Assignees: Shanghai Institute of Materia Medica, Chinese Academy of Sciences, Shanghai (CN); Shanghai Lead Discovery Pharmaceuticals Limited Company, Shanghai (CN)

( * ) Notice: Subject to any disclaimer, the term of this patent is extended or adjusted under 35 U.S.C. 154(b) by 671 days.

(21) Appl. No.: 11/293,847

(22) Filed: Dec. 2, 2005

(65) Prior Publication Data

US 2006/0142383 A1 Jun. 29, 2006

(30) Foreign Application Priority Data

Jun. 4, 2003 (CN) .................. 03 1 29071
Jun. 18, 2003 (WO) ............ PCT/CN03/00472

(51) Int. Cl.
*A61K 31/165* (2006.01)
(52) U.S. Cl. ...................................... 514/617
(58) Field of Classification Search ........... 514/617, 514/523, 534
See application file for complete search history.

(56) References Cited

U.S. PATENT DOCUMENTS 3,793,366 A * 2/1974 Krapcho ............... 560/104

FOREIGN PATENT DOCUMENTS

EP 1193257 4/2002

OTHER PUBLICATIONS

Jean Tirouflet, et al. "Synthesis and Physicochemical Properties of Substituted Phthalonimides," Chemical Abstracts Service, Columbus, Ohio, p. 1, 1958.

(Continued)

*Primary Examiner*—Shengjun Wang
(74) *Attorney, Agent, or Firm*—Baker & Hostetler LLP

(57) ABSTRACT

The present invention discloses 3D-structure of SARS-CoV Viral 3CL Protease obtained through molecular simulation. The 3D-structure is used as a drug target for screening the existing medical database CMC (Comprehensive Medicinal Chemistry, MDL Information System, Inc.), and a group of compounds which have the activity of inhibiting SARS-CoV virus 3CL Protease are found. Cinanserin was tested at molecular and viral levels, and it was found to be able to inhibit the SARS-CoV viral 3CL protease and SARS-CoV viruses. Cinanserin analogs were synthesized and tested at molecular and viral levels, they were found to be able to inhibit the SARS-CoV virus 3CL Protease and SARS-CoV viruses, and may be used for treating and/or preventing SARS-CoV virus infection.

1 Claim, 2 Drawing Sheets

OTHER PUBLICATIONS

Rene Dabard, "Condensation Products of Homophthalimides and Aromatic and Heterocyclic Aldehydes," Chemical Abstracts Service, Columbus, Ohio, p. 1, 1957.

Tetsuya Kita, et al. "Thymidine Phosphorylase Inhibitors with a Homophthalimide Skeleton," *Biological & Pharmaceutical Bulletin*, vol. 24, No. 7, pp. 860-862, 2001.

Glynn Mitchell, et al. "1,3,4(2H)-Isoquinolinetriones: Evaluation of Amino-Substituted Derivatives as Redox Mediator Herbicides," *Pest Management Science*, vol. 56, No. 2, pp. 120-126, 2000.

Ling Ke-Qing, et al. "On the Reactions of 1,3-Isoquinolinediones with Singlet Oxygen," *Tetrahedron*, vol. 55, No. 30, pp. 9185-9204, 1999.

Marco Mazza, et al. "Herbicidal Activity of 2-substituted 1,3,4-(2H)-isoquinolinetriones," *Farmaco*, vol. 54, No. 6, pp. 339-345, 1999; and American Chemical Society, Search Strategy (131:181047), 2002.

Ling Ke-Qing, et al. "Dye-Sensitized Photooxygenations of 1,3-Isoquinolinediones," *Tetrahedron Letters*, vol. 39, No. 16, pp. 2381-2384, 1999.

C. Pollers-Wieers, et al. "The Use of Isoquinolinetriones in the Synthesis of Benzo[c]phenanthridine Alkaloids," *Tetrahedron*, vol. 37, No. 24, pp. 4321-4326, 1981.

Jozef Vekemans, et al. "A New Pathway to 1,3,4(2H)-Isoquinolinetriones and Substituted Isoindolinones," *Tetrahedron*, vol. 36, No. 7, pp. 943-950, 1980.

N.P. Buu-Hoi, et al. "Phthalonimides (1,3,4-Trioxo-1,2,3,4-Tetrahydroisoquinolines) of Potential Biological Interest," *Journal of Heterocyclic Chemistry*, 5(4), pp. 545-547, 1968.

* cited by examiner

3D-STRUCTURE MODEL OF SARS CORONAVIRUS 3CL PROTEASE AND ANTI-SARS DRUGS

PRIORITY CLAIM

This claims priority under 35 U.S.C. §120 of International Patent Application No. PCT/CN2003/000472 filed on Jun. 18, 2003, which claims priority to Chinese Patent Application No. 03129071.X filed on Jun. 3, 2003, the teachings of both applications being incorporated in their entirety herein by reference.

FIELD OF THE INVENTION

The present invention relates to a method for screening drugs by modeling them to a drug target, particularly to a method for screening drugs on a molecular and viral levels with the 3D-structure model of SARS-CoV virus 3CL Protease ($3CL^{Pro}$) as the target for drug design, and to the use of cinanserin derivatives as the inhibitors of the SARS-CoV virus 3CL Protease and as the medicines useful to inhibit SARS-CoV viruses and in treating and/or preventing SARS viral infection in mammals.

BACKGROUND OF THE INVENTION

Infectious atypical pneumonia is referred to as Severe Acute Respiratory Syndrome (SARS). From the end of 2002 to the beginning of 2003, patients infected with SARS were initially found in the Province of Guangdong of China. Subsequently cases of SARS infections erupted in Hong Kong, Vietnam and Canada, and then spread to over 33 countries and regions. Moreover, SARS erupted in 27 provinces and cities of China, such as Beijing, the Shanxi province, and Mongolia Municipality. The SARS virus is a novel virus, which has strong infectivity and survivability, and high lethality. As of May 31, 2003, 8,360 people worldwide were infected by SARS, and the number of deaths reached 764. Thus, SARS seriously destroyed many people's lives and the economical foundation of the nation.

It has been found by studies that a novel coronavirus is likely to be the cause of SARS. The virus was isolated from the SARS patients and the cadavers of individuals who had been infected with SARS in Hong Kong and Canada, and the anti-hMPV antibody was also found in the serum of some SARS patients. On Apr. 16, 2003, the World Health Organization (WHO) formally confirmed that the SARS virus is the cause of the SARS. In SARS patients, around 90% of the SARS virus infected patients recover spontaneously, and about 10% of the remaining infected patients succumb to the disease. The electron microscope photographs of the respiratory tract slice and the cell culture from the SARS patients show the existence of the coronavirus virosomes. This is a novel type of coronavirus, different from the other known member of the coronavirus genus. This virus can cause a cytopathic effect to green-monkey kidney cells (VERO-E6). The virus replication can be inhibited by the serum recovered from SARS-infected people. And, the immunofluorescence assay (IFA) may be performed using the infected cells and the serum of the recovered people to detect the SARS virus infected cells in the cell culture. This method demonstrates a specific reaction. Studies from the U.S., Canada and Hong Kong show that the serum from non-SARS patients cannot react with this novel coronavirus; the super-antiserums for transmissible gastroenteritis virus (TGEV), murine hepatitis virus (MHV), feline infectious peritonitis virus (FIPV), and 229E human coronavirus may inhibit the growth of the cultured viruses. Virus sequencing conducted in several laboratories show that this novel virus relates to the coronavirus genus, but was different from the other coronavirus groups in the same genus, and is a new variation of the coronavirus. The SARS coronavirus is classified in the coronaviridae strain of nidovirales group of ssRNA positive strand viruses family by species and genus. And, it is a new sub-genus in the coronavirus family.

In March of 2003, scientists discovered the SARS Coronavirus (SARS-CoV), which is the true agent causing SARS, and successfully sequenced the entire SARS-CoV genome. The SARS-CoV genome is comprised of 29727 nucleotides and 11 opening reading frames. The structure of its genome is very similar to other coronaviruses. However, comparison of the genetic history to the sequences shows that the characteristics of SARS-CoV are not completely similar to those of the previously known coronaviruses, and the SARS-CoV has its own specific characteristics in addition to features in common with the other coronaviruses. See Paul A. Rota, M. Steven Oberste, Stephan S. Monroe, W. Allan Nix, Ray Campagnoli, et al. Characterization of a novel coronavirus associated with severe acute respiratory syndrome. Science (Sciencexpress) (May 1, 2003); Marco A. Marra, Steven J. M. Jones, Caroline R. Astell, Robert A. Holt, Angela Brooks-Wilson et al., The genomic sequence of the SARS-associated coronavirus, Science 300: 1394-1398 (2003). At the same time, the scientists performed the genome sequencing of 29751 bases of the Toronto Canada isolated strain (Tor2) of SARS-associated coronavirus. The genomic sequence indicated that this coronavirus didn't closely relate to the known coronavirus (including the human coronavirus HcoVOC43, HCoV-229E). The analysis for predicating the genus and species of the viral protein shows that this coronavirus is not closely related to the known three groups of coronaviruses. The genomic sequence will be helpful for people to understand the mechanism of SARS viral infection, diagnose and detect the latent animal host (using PCR method and immunological test), and also be assistant to develop the anti-virus preparation (including neutralizing antibody) and find the antigenic determinants of vaccine (Marco A. Marra, Steven J. M. Jones, Caroline R. Astell, Robert A. Holt, Angela Brooks-Wilson, et al., The genome sequence of the SARS-associated coronavirus, Science, 300:1399-1403 (2003).

Genomic sequencing and bioinformatics analysis has shown that the SARS-CoV virus is mainly comprised of the following functional proteins: a polymerase, a spike (S) glycoprotein, a small envelope (E) protein, a matrix (M) protein, a nucleocapsid (N) protein, and a 3C-like (3CL) protease. Theoretically, all of these proteins can be used as the target of drug design and drug screen for the anti SARS-CoV virus drugs. However, use of 3CL protease as the target in drug designing and screening has some particular advantages: (1) from the functions of 3CL proteases of other coronavirus, it is presumed that the SARS-CoV virus 3CL protease may play an important role during virus replication; (2) there are many 3CL protease inhibitors for other viruses, which can be directly experimented to inhibit the activity of SARS-CoV 3CL protease and in the anti-SARS-CoV test; (3) 3CL protease is very easy to express, so that the protein may be obtained in a short period to screen the drugs. And the screening model at the molecular level in the present invention was constructed just with the expressed SARS-CoV virus 3CL protease by the present inventors, and the protein expression process had been previously described in patent application no. CN 1468961 from the People's Republic of China; (4) SARS-CoV 3CL protease has the higher sequence homology with the main proteinases (M$^{pro}$) of the human coronavirus and the genetic gastroenteritis virus, and the 3D-structure of SARS-CoV virus 3CL protease can be constructed with the crystal structures of these two proteases as the templates to perform the design and virtual screening of the inhibitors.

Therefore, the first object of the present invention is to provide a 3D-structure model of SARS-CoV 3CL protease as a target of drug screening for the drugs for treating and/or preventing SARS-CoV viral infection.

The second object of the present invention is to provide a method for screening the drugs for treating and/or preventing SARS-CoV viral infection using the above drug target.

The third object of the present invention is to provide the drugs for treating and/or preventing SARS viral infection screened out using such a drug target.

SUMMARY

The present invention constructs a 3D-structure of SARS-Cov 3CL protease as the drug target for screening the anti-SARS-CoV viral drugs, and the discovery of drugs (compounds) which inhibit the SARS-CoV viral 3CL protease and inhibit SARS-CoV viruses from the present drug database through the computer virtual screening method, and then performs the protease molecule test and the SARS-CoV virus infected Vero-E6 cell test, to provide the drugs and medicinal composition for treating and/or preventing the SARS.

The target of anti-SARS-CoV virus drug provided by the present invention is the SARS coronavirus 3CL protease, having the sequences as follows: (SEQ ID NO:1)

```
  1 SGPRKMAFPS GKVEGCMVQV TCGTTTLNGL WLDDTVYCPR HVICTAEDML NPNYEDLLIR

61 KSNHSFLVQA GNVQLRVIGH SMQNCLLRLK VDTSNPKTPK YKFVRIQPGQ TFSVLACYNG

121 SPSGVYQCAM RPNHTIKGSF LNGSCGSVGF NIDYDCVSFC YMHHMELPTG VHAGTDLEGK

181 FYGPFVDRQT AQAAGTDTTI TLNVLAWLYA AVINGDRWFL NRFTTTLNDF NLVAMKYNYE

241 PLTQDHVDIL GPLSAQTGIA VLDMCAALKE LLQNGMNGRT ILGSTILEDE FTPFDVVRQC

301 SGVTFQ
```

The method for screening the inhibitors of SARS-CoV virus 3CL protease and/or the drugs for treating and preventing SARS virus infection provided by the present invention comprises the following steps:

1) Constructing a 3D-structure model of SARS-CoV viral 3CL protease;

2) Virtual screening and searching the present drug databases through molecule docking to obtain the candidate compounds having a stronger affinity to the 3CL protease;

3) Determining the kinetic parameters for the interaction of the 3CL protease and the above candidate compounds using the surface plasmon resonance technique (SPR);

4) Testing the protective effect of the candidate compounds against the SARS-CoV viruses' infecting cell.

The present invention also provides the inhibitors of the SARS-CoV virus 3CL protease, and the said inhibitors are the organic molecular compounds or the polypeptide compounds combining with the 3D-structure model.

The SARS-CoV viral 3CL protease inhibitors provided by the present invention can be used to prepare the medicines for treating and/or preventing SARS virus infection in a mammal, in particular a human.

The SARS-CoV virus 3CL protease inhibitors provided by the present invention can also be used to treat mammal, especially humans, infected with the SARS virus, or the protease inhibitors can be administered to a mammal, especially a human, to prevent infection SARS virus infection in a mammal, in particular a human.

The present invention further provides the cinanserin of the general formula I and the analogs thereof, or their pharmaceutical salts or hydrates for the treatment of mammals infected with the SARS virus or the prevention of the infection of the SARS virus in a mammal, particular a human, $$\text{(I)}$$

Wherein, $R^1$ is hydrogen, $C_1$-$C_4$ alkyl, substituted $C_1$-$C_4$ alkyl, hydroxyl, halogen, acetyl, substituted $C_1$-$C_4$ alkyl acyl;

$R^2$ is hydrogen, $C_1$-$C_4$ alkyl, substituted $C_1$-$C_4$ alkyl, hydroxyl, halogen, acetyl, substituted $C_1$-$C_4$ alkyl acyl;

$$R^3 \text{ is } -(CH_2)n-N\begin{smallmatrix}R^4\\R^5\end{smallmatrix}$$

Wherein n=1-4, $R^4$ and $R^5$ is hydrogen, $C_1$-$C_4$ alkyl, substituted $C_1$-$C_4$ alkyl, hydroxyl, halogen, acetyl, substituted $C_1$-$C_4$ alkyl acyl;

X is O, N or S;

Y is O, N, S, sulfoxide, or sulphonyl.

The cinanserin of the general formula I and the analogs thereof or their pharmaceutical salts or hydrates can be used to prepare the medicines for treating and/or preventing SARS virus infection.

Further, the present invention provide the medicinal composition for treating and/or preventing SARS virus infection, which comprises the cinanserin of the general formula I and the analogs thereof or their pharmaceutical salts or hydrates in an effective dosage for treating and/or preventing SARS virus infection, and at least one pharmaceutically acceptable carrier or excipient.

BRIEF DESCRIPTION OF THE DRAWINGS

FIG. 1b shows the protein 3D-structure model of SARS-CoV 3CL protease. The substrate couples to the groove between the structural domains I and II, the active site locates at the intermediate portion of the groove, and the catalyzing residues H41 and C145 are showed in the ball-stick model.

DETAILED DESCRIPTION

In the present invention, the 3D-structure of SARS-CoV viral 3CL protease was obtained through molecular modeling; and based on the 3D-structure of the SARS-CoV viral 3CL protease, 10 compounds which have the activity of inhibiting SARS-CoV viral 3CL Protease were found through screening the present medical database CMC (Comprehensive Medicinal Chemistry, MDL Information System, Inc.) by the virtual screening method; cinanserin (2'-(3-dimethylaminopropylthio)cinnamanilide) among these compounds was assayed on molecular and viral levels and found to be able to inhibit the SARS-CoV viral 3CL protease and the SARS-CoV virus. Cinanserin and its analogs were synthesized and assayed on molecular and viral levels, as a result it was discovered that this group of compound are a able to inhibit SARS-CoV viral 3CL Protease and to inhibit the SARS-CoV virus. The method to discover these anti-SAR-CoV virus compounds was done as follows.

1. Construct a 3D-structure model of the SARS-CoV virus 3CL Protease through molecule modeling and homological protein modeling.

The sequence analysis shows that SARS-CoV virus 3CL protease has a high sequence homology with the main proteinase (M$^{Pro}$) of the genetic gastroenteritis virus. In the full-length sequence comparison, the similarity of their sequence is more than 60%, the identity is more than 43%, and the sequence gap is less than 1%. A 3-D structure model is constructed by the homological protein modeling method with the crystal structure of M$^{pro}$ protein (Anand K, Palm G J, Mesters J R, Siddell S G, Ziebuhr J, et al. EMBO J 21:3213 (2002), the number of PDB: 1LVO) as the template, and the comparison of the structure model with the crystal structure of M$^{pro}$ protein is showed in the FIG. 1. The active center and the active pocket are established in the 3-D structure model of SARS-CoV viral 3CL protease.

2. Virtual Screening

Figure 2B:
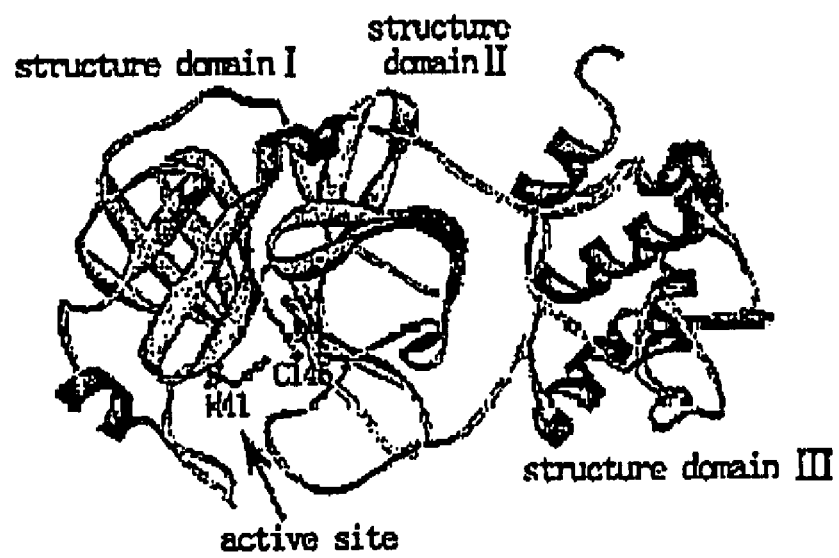
FIG. 2 is a superficial drawing of protein-substrate binding pocket of the 3CL protease. The shade depth of the color in the superficial drawing indicates the distribution of electrostatic potential. The deeper the color is, the more negative the electrostatic potential is. Cinanserin (showed by CPK model) is coupled into the binding pocket.
Figure 2:
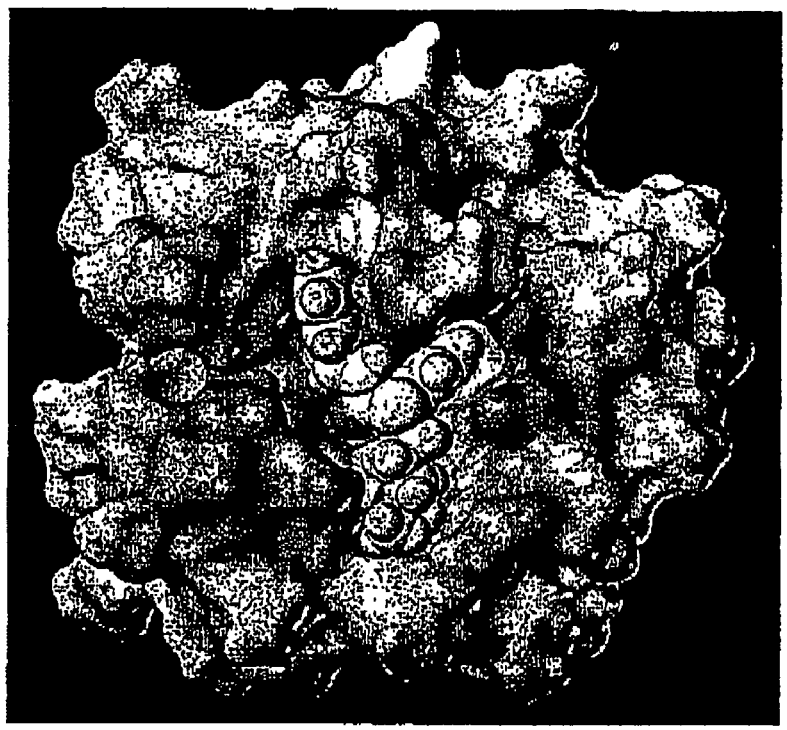

The substrate-binding pocket consisting of the residues within 6 Å from the catalyzing active residues H41 and C145 of the 3CL protease was used as the model for virtual screening, and the superficial drawing of the substrate binding pocket is shown in the FIG. 2. The medical database CMC of the MDL corporation was screened by molecular docking virtual screening method and a group of compounds having the stronger affinity to 3CL protease are obtained, including cinanserin (2'-(3-dimethylaminopropylthio)cinnamanilide). The binding manner of cinanserin with 3CL protease protein is shown in the FIG. 2.

3 Screening on the Molecule Level

E. coli. M15 was transformed with the constructed pQE30/SARS-3CL protease plasmid, and the SARS-CoV virus 3CL protease protein was expressed under the induction of IPTG (0.8 mM) with ampicilin as antibiotic at 30° C. for 10 hours. The SARS-CoV virus 3CL protease protein was primarily purified by the NTA-His column chromatography method, and was further purified with the FPLC-gel filtration.

Figure 3:
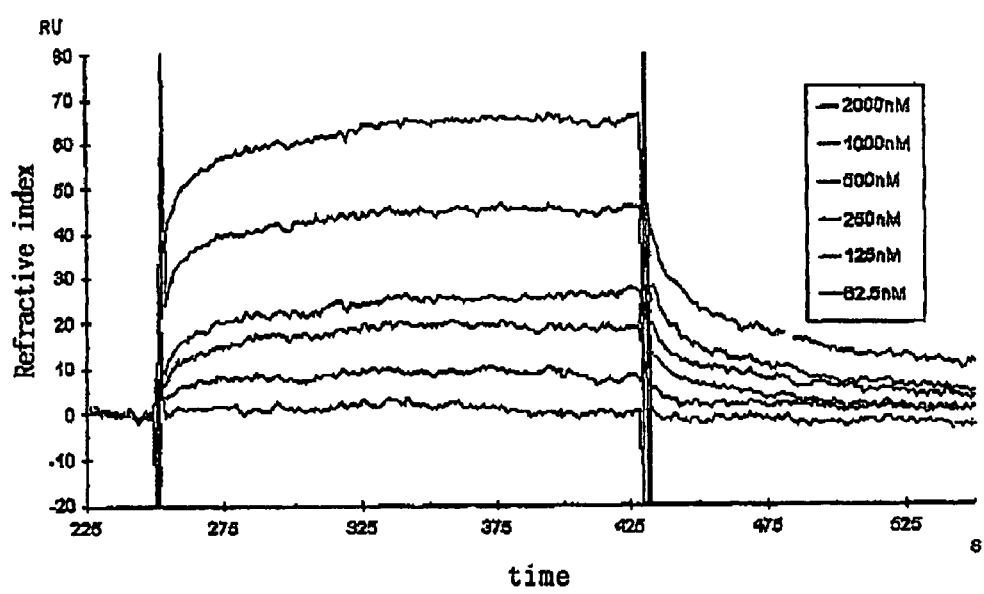
FIG. 3 shows the kinetics testing result of the interaction of SARS-CoV virus 3CL protease protein and cinanserin. The analytical instrument was BIACORE3000, and the analytic software was Kinetic Analysis of Application Wizard. During testing, the 3CL protease protein was fixed on a CM5 chip, and cinanserin was used as the mobile phase with the concentration of 62.5 nM, 125 nM, 250 nM, 500 nM, 1000 nM and 2000 nM in turn.

The kinetic parameters for the interaction of the SARS-CoV virus 3CL protease protein and the above candidate compounds obtained through virtual screening were obtained using the surface plasmon resonance (SPR) technique. The kinetic parameters for the binding of cinanserin and 3CL protease protein is: $k_a=3.86\times10^4$ Ms$^{-1}$, $k_d=9.93\times10^{-3}$ s$^{-1}$, $K_D=2.57\times10^{-6}$M, showing a stronger binding of the SARS-CoV virus 3CL protease protein and cinanserin. The test results are showed in the FIG. 3.

4. Screening on the Virus and Cell Levels

To determine whether cinanserin can inhibit the SARS-CoV virus from infecting a normal cell, in the present invention, the activity of cinanserin for inhibiting the SARS-CoV virus from infecting the Vero-E6 cell was tested.

Testing Principle: the protective effect of a sample compound against the virus infection of the cell was determined using Vero-E6 cell as the host cell (susceptible cells), and the testing indicators were cytopathic effect (CPE) and the observing protective ratio of the infected cells.

Testing Method: Vero-E6 cells were inoculated into a 96-well plate, which was placed into the incubator with 5% CO$_2$ at 37° C. SARS-CoV virus and cinanserin of different diluting concentrations were added. CPE was observed, and OD values were determined by dying with the neutral red. The effect of sample's anti-SARS-CoV virus activity was calculated.

Testing Result: in the assay of anti-SARS virus activity with the model on the virus-cell level, Vero-E6 cell was infected with SARS viruses in different effective concentrations, and the results listed in the table 1 show that cinanserin has the evident protective activity of inhibiting SARS-CoV from infecting Vero-E6 cell.

TABLE 1

The protective ratio of cinanserin in different concentrations for protecting Vero-E6 cell from SARS-CoV virus infection

| Concentration (ug/mL) | CPE | Protective ratio of the infected cells (times) |
|---|---|---|
| 100 | — | —* |
| 20 | + | 3.85 |
| 4 | + | 3.69 |

Cytophatic effect (CPE): "+" represents the cytopathic degree, <25% +, 25%~50% ++, 50%~75% +++, >75% ++++

Protective ratio of the infected cells: the protective activity of the sample on the infected cells was calculated by comparing the OD values of the virus control, the cell control, and the sample control. If the protective ratio is >1.5 times, it may be primarily judge the sample having a certain activity of protecting the cell from viral infection.

*Cytotoxicity of the sample: if the cytotoxicity of the sample is >50% when comparing with the cell control, CPE isn't evaluated, and the protective ratio isn't calculated.

5. The Novel Use of Cinanserin and its Analogs for Anti-SARS-CoV Virus

Cinanserin is an old medicine developed in 1960', and was initially found to be an antagonist of the 5-HT receptor and used for hypnogenesis or prolonging the sleeping time, and had an analgesia effect (Furgiuele A R, High J P, Horovitz Z P. Arch. Int. Pharmacodyn. Ther., 1965, 155:225-235; Krapcho J, Rubin B, et al. J. Med. Chem. 1963, 6:219; Rubin B, Piala J J, et al, Arch. Int. Pharmacodyn. Ther. 1964, 152: 132). Later, it was found that cinanserin and its analogs had immunologically inhibiting effect (Krapcho J, Millonig R C, et al. J. Med. Chem. 1969, 12: 164); and it was also found that this group of compounds had an anti-inflammation effect (Millonig R C, Amrein B J, et al. J. Med. Chem. 1974, 17:772). Cinanserin had been applied to the clinical research as an anti-chronic schizophrenia medicine (Holden J M C, Itil T. et al, J. Clin. Pharmacol. New Drugs 1971, 11: 220; Itil T M, Polvan N, Holden J M. Dis. Nerv. Syst. 1971 32: 193; Gallant D M, Bishop M P. Curr. Ther. Res. Clin. Exp. 1968 10: 461). And in 1990s, cinanserin was developed into a medicine for treating myocardial ischemia (EP0596449). However, it is never reported that cinanserin and its analogs are able to inhibit the SARS-CoV viral 3CL protease or to inhibit the SARS-CoV virus.

The present invention relates to the activity of cinanserin inhibiting the catalyzing activity of SARS-CoV viral 3CL protease, and its new anti-SARS-CoV viral activity. Based on the 3D-structure of SARS-CoV virus 3CL protease protein, the compound capable of inhibiting the catalyzing activity of the SARS-CoV viral 3CL protease, cinanserin, was screened out by virtual screening, and the compound of the general formula I and the analogs thereof were synthesized. Through the activity test of SPR on molecular level and the activity test of inhibiting the virus from infecting Vero-E6 cell, it was found that the cinanserin of the general formula I and the analogs thereof bind specifically to the SARS-CoV viral 3CL protease protein, and have the evident protective activity of inhibiting the SARS virus from infecting Vero-E6 cell, and thus have the new use for treating and/or preventing SARS-CoV viral infection.

Each substituent of the cinanserin derivatives of the general formula I or the pharmaceutically acceptable salts or hydrates thereof are defined as follows:

(I)

in which, $R^1$ is hydrogen, $C_1$-$C_4$ alkyl, substituted $C_1$-$C_4$ alkyl, hydroxyl, halogen, acetyl, substituted $C_1$-$C_4$ alkyl acyl;

$R^2$ is hydrogen, $C_1$-$C_4$ alkyl, substituted $C_1$-$C_4$ alkyl, hydroxyl, halogen, acetyl, substituted $C_1$-$C_4$ alkyl acyl;

$R^3$ is —$(CH_2)n$—N$\langle{}^{R^4}_{R^5}$

Wherein n=1-4, $R^4$ and $R^5$ is hydrogen, $C_1$-$C_4$ alkyl, substituted $C_1$-$C_4$ alkyl, hydroxyl, halogen, acetyl, substituted $C_1$-$C_4$ alkyl acyl;

X is O, N or S;

Y is O, N, S, sulfoxide, or sulphonyl.

Particularly, the examples of said "pharmaceutical salts" in the present description include the salts formed from the esters, which are obtained from cinanserin derivatives with the organic acids, such as propionic acid, oxalic acid, malonic acid, succinic acid, fumaric acid, maleic acid, lactic acid, malic acid, tartaric acid, and citric acid etc., and the acidic amino acids, such as aspartic acid, and glutamic acid etc., with the inorganic alkalis, such as the sodium salt, potassium salt, calcium salt, aluminum salt, and amide salt, or with the organic alkalis, such as methyl amine salt, ethyl amine salt, or ethanolamine salt etc.; or the salts formed from the esters, which are obtained from cinanserin derivatives with the basic amino acids, such as lysine, arginine, ornithine etc., with the inorganic acids, such as the hydrochloric acid, hydrobromic acid, hydrofluoric acid, sulfuric acid, nitric acid, and phosphoric acid etc., or with the organic acids, such as formic acid, acetic acid, picric acid, methyl sulfonic acid, and ethyl sulfonic acid etc.

Preferably, the compound of the general formula I or the pharmaceutical salts or hydrates thereof include cinanserin (2'-(3-dimethylaminopropylthio)cinnamanilide).

Another aspect of the present invention relates to the medicinal composition for treating and/or preventing SARS virus infection, which comprises cinanserin of the general formula I and the analogs thereof, or their pharmaceutical salts or hydrates in an effective dosage for treating and/or preventing SARS virus infection, and at least one pharmaceutically acceptable carrier or excipient.

The said pharmaceutically acceptable carrier or excipient herein includes, but not limit to: ion exchanger, alumina, stearic aluminum, lecithin, serum protein such as human albumin, buffer substance such as phosphate, glycerol, sorbic acid, potassium sorbic acid, the mixture of part glyceride of the saturated plant fatty acid, water, salt or electrolyte such as protamine sulphate, disodium hydrogen phosphate, potassium hydrogen phosphate, sodium chloride, zinc salt, colloidal silicon oxide, magnesium trisilicate, polyvinylpyrrolidone, cellulose substance, polyglycol, sodium carboxymethyl cellulose, polyacrylate, beeswax, and lanoline.

The present invention also relates to the new use of the compound represented by the general formula I or the medicinal composition comprising the compound of the general formula I or the pharmaceutical salts or hydrates thereof for preparing the medicines for preventing and/or treating Severe Acute Respiratory Syndrome (SARS).

The said medicinal composition may be formulated into various dosage forms according to the different administration routes. The said dosage forms may be applied through one of the following routes: oral administration, spray inhaling, rectal administration, nasal cavity administration, general administration, local administration, non-enteric administration, such as subcutaneous, venous, intramuscular, peritoneal, thecal, cardiac ventricle, internal and encephalic injection or transfusion, or administration with aid of a explanted storage unit. In case of preventing SARS virus infection, oral administration or muscular injection is preferable, and in case of treating SARS virus infection, peritoneal or venous administration is preferable.

Furthermore, the dosage and administration route of the compound of the present invention depend on many factors, including the patients' age, weight, gender, natural healthy condition, nutrient condition, and the activity strength of the compound, administration time, metabolizing rate, the severity of the illness condition, and the physician's judgment.

The inhibitor of SARS-CoV virus 3CL protease protein in the present invention blocks the replication, transcription, translation and assembly of SARS virus, and blocks the maturation of the virus and the formation of the virusome. The blocking of the inhibitor of 3CL protease protein in SARS-CoV virus infection has no adverse effect on the normal physiological process of the patients or animals infected by SARS virus, So they can be applied to treat and/or prevent SARS infection.

Preferred Embodiments

The following examples are illustrative of the preferred embodiments of the present invention, but are not meant to limit the claimed invention in any way.

EXAMPLE 1

Modeling of the 3D-Structure of SARS-CoV Virus 3CL Protease

The compared sequences were provided by US National Center of Bioinformatics (NCBI), and are respectively derived from the specimens of SARS patients from the different regions, including the NCBI registry number of gi|30275668(BJ01), gi|30027618(Vietnam), gi|29836495 (Tor2), gi|30023962(CUHKW1), gi|29837498(GZ01), gi|30275667(BJ02), gi|30023953(HKU-39849), gi|30124074(Canada), and gi|30173234(BJ03). The multiple sequence comparison was performed with the Clustal X (Version 1.8) method, and the results show that all of the sequenced SARS-CoV viruses have the identical 3CL protease protein sequences.

Figure 1A:
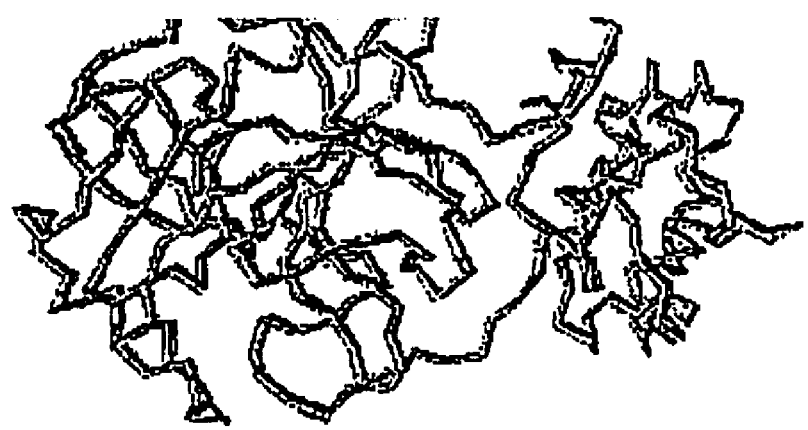
FIG. 1a shows the superimposition of the 3D-structure model of SARS-CoV 3CL protease (light-color) and the crystal structure of TGEV M$^{pro}$ protein (dark-color), in which only C$^{\alpha}$ atoms are displayed, and the RMSD of the whole structural superimposition is 0.34 Å.

The protein sequence of SARS-CoV virus 3CL protease has a high sequence homology with the main proteinase ($M^{pro}$) of the genetic gastroenteritis virus, and according to the result of their full sequences comparison, the similarity of their sequences is over 60%, the identity is over 43%, and the sequence gap is less than 1%. The 3D-structure model was constructed by the homological protein modeling method using the crystal structure of the $M^{pro}$ protein (Anad K, Palm G J, Mesters J R, Siddell S G, Ziebuhr J, et al. EMBO J 2002, 21: 3213, PDB No.: 1LVO) as the template. The 3D-structure modeling used the MODELLER software of Insight II, and 3D-Profile and Prostat softwares were used to evaluate the quality of the structure model. The primary structure of the composition was obtained and then optimized with molecular dynamics with force field parameters of Amber force field and Kollman-all-atom charge. The structure model and the comparison with the crystal structure of $M^{Pro}$ are shown in FIG. 1.

EXAMPLE 2

The Virtual Screening of the Inhibitor of the SARS-CoV Virus 3CL Protease

The present CMC database of MDL cooperation, including the information of total 8474 known drugs, was screened by molecular docking method using the DOCK program. Upon molecular docking, the flexibility of the small molecular compound was considered, and 10 candidates compounds were chosen out from the above database according to their scores and further evaluated with the AutoDock scoring function and the Cscore scoring function. Cinanserin was finally selected for screening on the molecule level.

EXAMPLE 3

The Kinetic Test on Binding of the Cinanserin with the SARS-CoV Virus 3CL Protease Protein The latent inhibitor of 3CL protease protein, cinanserin, was selected through virtual screening and testing on the molecule level. In this example, the process of the kinetic test on binding of the inhibitor (cinanserin) and 3CL protease protein was illuminated. The 3CL protease protein was fixed on a CM5 chip, and the cinanserin was the mobile phase. The kinetic behaviors of the cinanserin and the 3CL protease protein were determined using BIACORE3000. The concentrations of the 3CL protease protein were 62.5 nM, 125 nM, 250 nM, 500 nM, 1000 nM, and 2000 nM in turn. The data were analyzed using Application Wizard/Kinetic Analysis softwares (FIG. 2), and the binding kinetic parameters between them were:

$$k_a=3.86\times10^4 Ms^{-1}, k_d=9.93\times10^{-3}s^{-1}, \text{ and } K_D=2.57\times10^{-6}M.$$

EXAMPLE 4

The Test of Cinanserin Protecting the Vero-E6 Cells from SARS-CoV Virus Infection The Vero-E6 cells were used as the host cells of the virus (susceptible cell) to test the protective effect of the sample on virus infecting. The testing indicators were the cytopathic effect (CPE) and the protective ratio of the infected cells.

The Vero-E6 cells were inoculated into a 96-wells plate, which was placed into the incubator with 5% $CO_2$ at 37° C. The SARS viruses and cinanserin of different diluting concentrations were added respectively, and the virus control, cell control and sample control groups were provided. The results were observed with the microscope every day, and CPE were recorded, the OD values were determined by dying with neutral red. The anti-SARS virus activities of the samples were calculated and evaluated with reference to the control groups. The testing results are showed in the Table 1.

EXAMPLE 5

The Synthesis of 2'-(3-dimethylaminopropylthio)anilide 54.0 g (1.0 mol) of sodium methanol in 500 ml of isopropyl alcohol was added into 1000 ml mixed solution of 62.5 g (0.5 mol) of 2-aminothio phenol in isopropyl alcohol. After stirring for 30 minutes at the room temperature, 79.0 g (0.5 mol) of 3-dimethylaminopropylchloro hydrochloride in 300 ml of toluene solution was added, and the mixed solution is refluxed for 6 hours. The solvents were removed with vacuum pump, 60 mL of water was added, and then the resultant was extracted twice with ether (150 ml×2). The organic phases were added up and were dried with the anhydrous magnesium sulphate. The solvents were removed through rotation evaporation. The product was rapidly separated by silica gel plate with ethyl acetate (1):oil ether (4)/dichloromethane (10): methanol (1) as the developing solvent to obtain 80.0 g of the oily product (76%).

EXAMPLE 6

The Synthesis of 2'-(3-dimethylaminopropylthio)cinnamanilide 5.2 g (0.025 mol) of 2-(3-dimethylaminopropylthio) anilide in 10 moles of chloroform was added drop-wise into 4.1 g (0.025 moles) of cinnhyl chloride in 30 mL of chloroform at 15 to 20° C. for about 20 minutes while stirring. The mixture was refluxed for 1 hour, and the solvents were removed under depression to obtain a viscous substance. The resultant product was thermally dissolved in acetone, allowed to stand for cooling, and filtered under reduced pressure to obtain 7.5 g of the colorless solid (88%), m.p. 109-111° C. The resultant solid was re-crystallized with isopropyl alcohol. The melting temperature of the product was 142-144° C.

What is claimed is:

1. A method for treating SARS in a mammal comprising administering cinanserin to said mammal.

* * * * *